United States Patent [19]
Liu

[11] Patent Number: 5,898,310
[45] Date of Patent: Apr. 27, 1999

[54] DEVICE AND METHOD FOR DETERMINING PROPERTIES OF A SOIL

[76] Inventor: Jin-Chen Liu, Mas-Liebermann-Strasse 6, 85221 Dachau, Germany

[21] Appl. No.: 08/898,718

[22] Filed: Jul. 22, 1997

[30] Foreign Application Priority Data

Jul. 23, 1996 [DE] Germany ............................. 19629745

[51] Int. Cl.⁶ .................................................. G01R 27/26
[52] U.S. Cl. ......................... 324/690; 324/664; 324/689; 324/696; 73/73
[58] Field of Search ..................... 324/663, 664, 324/686, 689, 690, 696, 634, 640, 643, 450; 73/73

[56] References Cited

U.S. PATENT DOCUMENTS

| | | | |
|---|---|---|---|
| 3,581,197 | 5/1971 | Morey et al. | 324/690 |
| 3,968,428 | 7/1976 | Numoto | 324/696 |
| 4,137,931 | 2/1979 | Hasenbeck | 324/689 |
| 4,929,885 | 5/1990 | Dishman | 324/690 |
| 5,087,886 | 2/1992 | Mann | 324/696 |
| 5,179,347 | 1/1993 | Hawkins | 324/696 |
| 5,260,666 | 11/1993 | Dishman et al. | 324/690 |
| 5,424,649 | 6/1995 | Gluck et al. | 324/690 |

FOREIGN PATENT DOCUMENTS

| | | |
|---|---|---|
| 1 673 046 | 8/1971 | Germany . |
| 2 004 142 | 8/1971 | Germany . |
| 30 11 420 A1 | 10/1981 | Germany . |
| 39 11 151 A1 | 10/1990 | Germany . |
| 148331 A1 | 6/1989 | U.S.S.R. . |

OTHER PUBLICATIONS

Miller, J.D. and G.J. Gaskin, "The Development and Applicaiton of the ThetaProbe Soil Water Sensor," Macaulay Land Use Research Institute, Aberdeen U.K. AB 15 8GH.(undated).

Fundinger, R. and K. Köhler, "messung der Material—und Bodenfeuchte mit der TRIME–Methode," Fa. IMKO GmbH, Ettlingen, 1992–1993. (month unavailable).

*Primary Examiner*—Diep N. Do
*Attorney, Agent, or Firm*—Seed and Berry LLP

[57] ABSTRACT

A measuring instrument for measuring the matrix potential in a soil, has a measuring cell with a housing that includes at least in certain sections thereof, material permitting the moisture of the soil to penetrate into the interior of the housing, at least two electrodes which are arranged in said housing in spaced relationship with each other and a dielectric which fills the space between said electrodes and the inner wall of the housing, a measurement evaluation circuit which detects the water content in the dielectric of the measuring cell by measurement of changes of permittivity of the dielectric and determines, on the basis of said water content and on the basis of a known relationship between the water content and the matrix potential of the dielectric used, the matrix potential prevailing in the dielectric, and which displays said matrix potential as a measuring result.

17 Claims, 2 Drawing Sheets

DEVICE AND METHOD FOR DETERMINING PROPERTIES OF A SOIL

TECHNICAL FIELD

The present invention relates to a device and method for determining properties of a soil, especially for determining the matrix potential in the soil.

BACKGROUND OF THE INVENTION

The term matrix potential of the soil describes the force per unit area with which the water contained therein is bound. The matrix potential is therefore normally given in the unit Pascal with a negative sign. However, also the term "extraction potential" ("Saugapannung"), which is given with a positive sign, is frequently used.

DE 39 11 151 A1 discloses a device that can be used for measuring the matrix potential in the soil. This device consists essentially of a tubular and gastight measuring cell which is to be inserted in the soil. The measuring cell is initially filled with water which, when said measuring cell has been inserted in the soil, leaks into the soil through a porous, liquid-permeable section of the measuring cell in accordance with the matrix potential prevailing in the soil. Due to the fact that part of the water leaks out of the measuring cell, a measurable negative pressure is generated in said measuring cell and this negative pressure is used as a measure of the matrix potential prevailing in the soil.

German-Offenlegungsschrift 16 73 046 discloses a device by means of which the soil moisture can be measured. The device comprises a measuring cell which is to be inserted in the soil and which has arranged therein electrodes separated by a dielectric having a known porosity and pore size. The capacitance prevailing between the electrodes, whose magnitude is determined by the nature of the dielectric used, is evaluated by an adequate measurement circuit. In view of the fact that soil moisture penetrates into the dielectric, the effective permittivity ratio or dielectric constant, which determines the capacitance, is changed. The determinable change of capacitance is regarded as a measure of the moisture in the soil. The dielectric provided in the measuring cell preferably consists of ceramics.

It is known that, especially in the field of agriculture, it is more important to measure the matrix potential of a soil than to measure of the moisture thereof A fine-grained soil consisting of a specific material has, due to a larger volume-absorbing surface per unit volume, a better capability of binding the water contained therein than a soil consisting of the same material but having a larger grain size. Provided that both types of soil contain the same amount of moisture, plants in the soil having the larger grain size will be able to absorb the water contained in said soil more easily.

The device known from DE 39 11 151 A1 is therefore more suitable for agricultural applications than the device known from German-Offenlegungsschrift 16 73 046. The device known from DE 39 11 151 A1 is, however, based on a principle permitting a determination of the matrix potential essentially only in a measurement change between 0 to approx. −800 Pascal, this being a range that exists only in the case of very wet soils.

SUMMARY OF THE INVENTION

It is therefore the object of the present invention to provide a device as well as a method by means of which the matrix potential of a soil can he measured simply and exactly.

This object is achieved by the subject matters of patent claims 1, 7 and 15.

Preferred embodiments of the present invention are the subject matters of the subclaims.

The present invention is based on the finding that, in spite of its dependence on the water content in the soil, the matrix potential of a soil can be determined reliably when a dielectric for which the connection between matrix potential and water content is known is used for the measurement.

The effective permittivity ratio or dielectric constant of the dielectric contained in the measuring cell is influenced by the water content entering the dielectric due to the moisture in the soil. This change of permittivity can be measured by a suitable measurement circuit and, on the basis of this measurement, conclusions can be drawn with regard to the water content of the dielectric. In view of the fact that the connection between water content and matrix potential is known for the dielectric used, this will also permit conclusions with regard to the matrix potential prevailing in the soil, since, for reasons of equilibrium, this matrix potential corresponds to that prevailing in the dielectric.

DETAILED DESCRIPTION OF THE INVENTION

Figure 1:
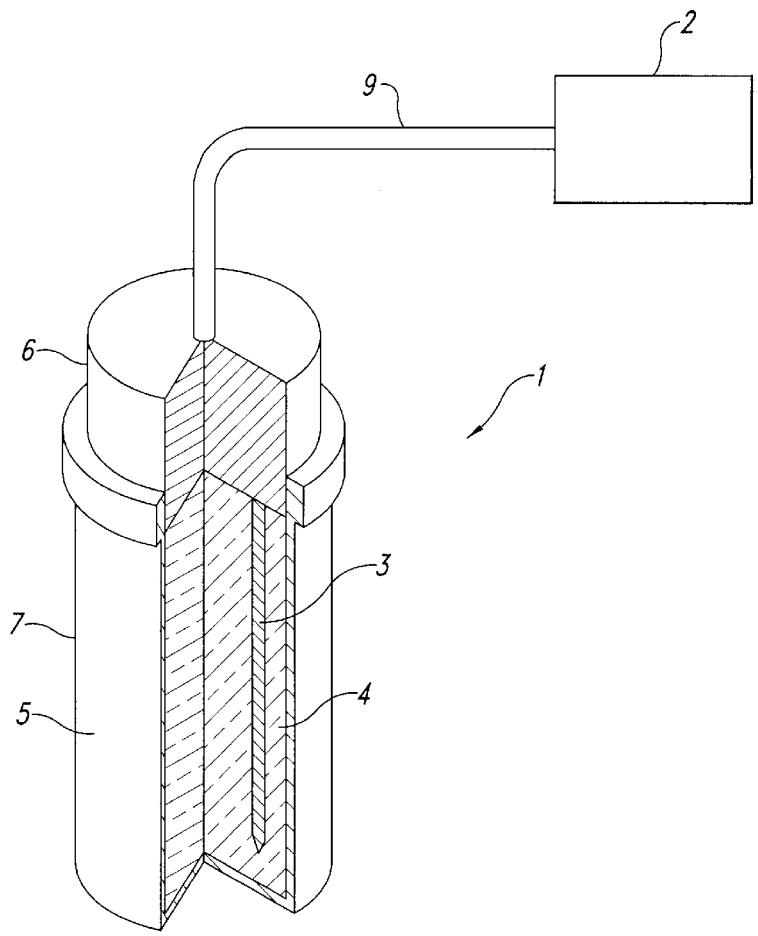
FIG. 1 is a schematic representation of a preferred embodiment of the measuring instrument according to the present invention.
Figure 2:
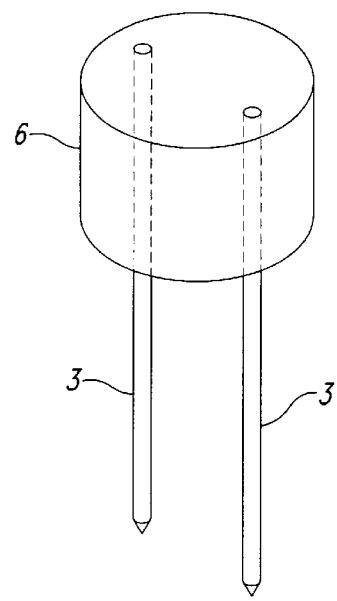
FIGS. 2 and 3 are schematic representations of a preferred structural design of the measuring cell.

FIG. 1 shows schematically a possible embodiment of the measuring instrument according to the present invention. The measuring instrument comprises a measuring cell or probe 1 as well as an evaluation circuit 2, said units being interconnected by a connection line 9. In the embodiment according to FIG. 1, the measuring cell 1 has a cylindrical shape and contains, as can be seen more clearly in FIG. 2, at least two electrodes 3. The outer shape of the measuring cell as well as the shape and the number of electrodes can, however, be designed in an arbitrary manner within wide limits, as will be recognized by the person skilled in the art. The electrodes 3 are arranged in spaced relationship with each other and they are embedded in a dielectric 4. The measuring cell additionally comprises a housing 5 consisting at least in certain sections thereof of a material permitting water or water vapour to penetrate into the interior of the cell from outside. A material suitable for this purpose is, e.g., polyamide or nylon. Hence, at least the part of the housing surrounding the dielectric 4 consists of a polyamide net.

As can be seen from FIG. 1, the measuring cell consists preferably of two sections. A lower section 7 accommodating therein the electrodes and the dielectric and an upper section 6 which preferably carries the electrodes and in the interior of which an electric circuit is provided, said electric circuit being used for signal detection. The size of the upper section 6 of the measuring cell can be large enough for accommodating therein the whole electric evaluation circuit so that an external evaluation circuit 2 of the type shown in FIG. 1 is no longer necessary.

Figure 3:
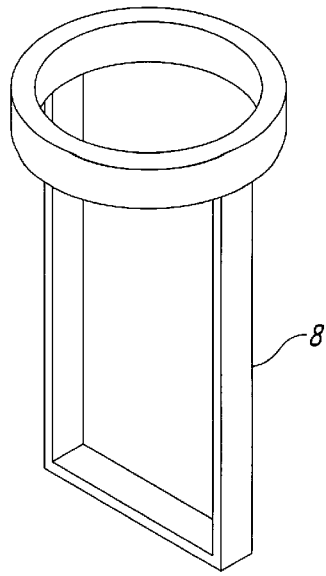

As can be seen in FIG. 3, especially the lower section 7 of the measuring cell can be defined by a frame 8 carrying the polyamide net 5 which forms the outer skin.

The dielectric 4 used preferably has a permittivity ratio or relative dielectric constant which is smaller than or equal to 81. A suitable material is therefore, e.g., quartz that can be filled into the interior of the measuring cell in the form of quartz sand. In order to achieve the best possible measuring result it should be taken care that the dielectric surrounds the electrodes without any gaps, i.e., without forming interspaces.

The electric circuit provided in the evaluation circuit 2 and/or in the upper section 6 of the measuring cell must be designed such that a change in the permittivity of the dielectric 4 caused by water penetrating from the soil into the cell can be detected. From the point of view of measurement, the change in permittivity is preferably detected through a change in the capacitance of the capacity defined by the electrodes. A permittivity ratio of less than or equal to 81 should be chosen because the permittivity ratio of water is approx. 81. The smaller the permittivity ratio of the dielectric 4 used is the greater the influence of the incoming water on the actually effective permittivity ratio will be.

From the point of view of measurement, the change of permittivity caused by the water penetrating from outside can be detected as a change of amplitude, a change of frequency or a change of the velocity of propagation of the electromagnetic field in the dielectric.

The measurement of the change of permittivity through a change of the velocity of propagation of an electromagnetic field in the dielectric is generally referred to as Time Domain Reflectrometry (TDR). Expressed simply, an electromagnetic wave will be transmitted along the electrodes 3 of FIG. 1 in the case of this measurement mode, said electromagnetic wave being then reflected in accordance with the laws of high-frequency technology. The period elapsing between the transmission of the pulse and the reception of the reflected pulse constitutes a measure of the velocity of propagation of the wave in the dielectric. In a material having a high dielectric constant, electromagnetic waves propagate less fast than in materials having a low dielectric constant. A dielectric having a high water content will therefore cause a longer transit time of the wave than the same dielectric in a dry condition. These transit time differences can be evaluated as a measure of the change in the overall permittivity and, consequently, as a measure of the existing water content. The circuits required for this purpose are well known to the person skilled in the art, and so are the circuits for measuring a change of capacitance caused by said change of permittivity; these circuits are therefore not described in detail.

Figure 4:
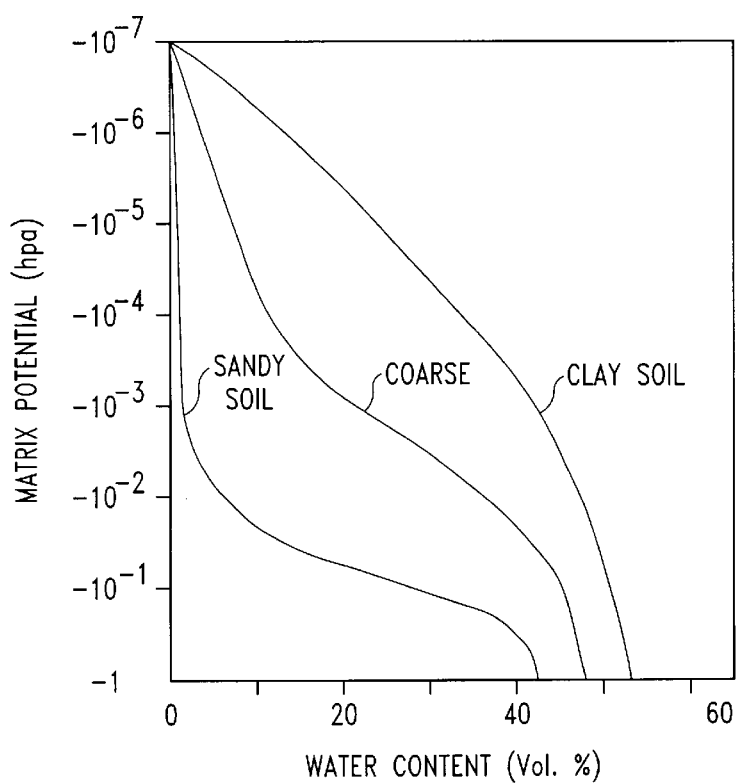
FIG. 4 is a schematic connection between the water content and the matrix potential for various materials.

FIG. 4 illustrates the fundamental connection between the matrix potential and the water content of the soil or of a water-absorbing material. Such curves are normally referred to as so-called pf curves. As can be seen, the matrix potential decreases as the water content increases. This means that a moist soil will bind the water contained therein less strongly than a soil having a lower moisture content. In a specific type of soil, plants can take up water more easily when this soil already has a high moisture content.

FIG. 4 shows pf curves for sandy soil, coarse or poor clay and clay soil.

The water content is indicated in percent by volume, the matrix potential in hpa.

According to the present invention, the material used for the measuring cell is a dielectric 4 with regard to which the fundamental connection between matrix potential and water content, which is shown in FIG. 4, is known. When the measuring cell has been implanted in the soil, the effective permittivity of the dielectric 4 will change due to the incoming water. In view of the fact that this change of permittivity can be detected by measurement with the aid of the above-mentioned evaluation circuit, it is also possible to detect the water content of the dielectric in this way. Especially in cases where the permittivity ratio of the dielectric 4 is much smaller than that of water, the actually effective permittivity is predominantly determined by the incoming water in soils having a sufficiently high moisture content. In view of the fact that, on the basis of measurements, conclusions can be drawn with regard to the water content existing in the dielectric 4, it is also possible to draw conclusions with regard to the instantaneous matrix potential in the dielectric 4 on the basis of the known correlation between water content and matrix potential for the dielectric 4. This matrix potential corresponds to the matrix potential prevailing in the soil outside of the measuring cell, since otherwise there would be no equilibrium. It follows that the matrix potential in the soil can be measured through the change of the permittivity of the dielectric 4.

By means of the present invention, a measuring range between 0 and −40 Megapascal can be detected. Although up to now "soil" has always been referred to, it is obvious that the present invention can also be used in a laboratory with arbitrary water-absorbing materials.

A field where the present invention can be used in a particularly advantageous manner is agriculture where it can be used for continuously supervising the matrix potential prevailing in the ploughland. The measuring instrument according to the present invention can be used in connection with a regulating system, which, when a specific predetermined matrix potential in the soil is exceeded, causes automatic irrigation of the soil. This will guarantee that the matrix potential in the soil is always maintained in a range permitting the plants to take up water and nutrients in the best possible manner.

A further important field of use of the present invention are environmental tests concerning the transport of water and substances in the soil. When the matrix potential distribution in the soil is known, conclusions can be drawn with regard to the distribution of the water entering the soil. If the water soaking into the soil carries contaminants, this also permits conclusions with regard to the distribution of contaminants in the soil.

The material used as a dielectric should have a large water-absorbing surface, if possible, whereby the resolution will be improved. The saturation humidity of the material should be higher than 30 percent by volume, if possible.

In addition, the material preferably includes a continuous, interconnected system of pores. This permits fast equalization of the matrix potential within the material and of that within the soil to be measured. The system of pores should be permeable to water as well as to air and water vapour. A fast equalization of the matrix potential will in this way also be possible in the dry condition, when the water moves in the soil predominantly in the gaseous state.

The dielectric 4 of the measuring cell 1 shown in FIG. 1 is preferably adapted to be exchanged for different measuring ranges. For example, for carrying out measurements in dry soil a dielectric may be used that is different from the dielectric used for measurements in humid soil. In view of the fact that the connection between water content and matrix potential, which is shown in FIG. 4, must be known for the respective dielectric so as to permit conclusions to be drawn with regard to the matrix potential on the basis of the measured change of permittivity, suitable reference values for the different dielectrics must he stored in advance in this case and must then be read out in accordance with the dielectric used. A measuring arrangement of this type works preferably digitally so that the individual curves for the different dielectrics to be used are stored in advance as digital values. It goes without saying that a completely analogue evaluation is, however, possible as well, in particular if only one dielectric is used.

The electrodes 3 of the measuring cell according to FIG. 1 are preferably coated with an insulating layer so as to prevent a flow of current between the electrodes. Notwithstanding this, the electric conductivity caused by the water content within the dielectric may perhaps influence the measuring result. Hence, it is important that the previously known connection between the water content and the matrix potential of the dielectric used has especially been ascertained for the concrete dielectric used as well as for the structure of said dielectric.

Although it has been assumed up to now that an equilibrium between the matrix potentials in the measuring cell and that in the soil already exists, it is clearly evident that the measurement can also be carried out in a sufficiently precise manner on the basis of the velocity with which the matrix potential changes in the dielectric. This will be advantageous for fast measurements and especially in cases where the water content in the soil varies greatly.

It should be understood that even though numerous advantages of the present invention have been set forth in the foregoing description, the above disclosure is illustrative only. Changes may be made in detail and yet remain within the broad principles of the present invention.

I claim:

1. A method of measuring a matrix potential in a soil having moisture and a matrix potential comprising the following steps:

inserting a measuring cell having an interior into the soil to be measured, said measuring cell permitting, at least in certain sections thereof, the moisture of the soil to penetrate into the interior of the measuring cell, and said measuring cell including in the interior thereof at least two electrodes embedded in a dielectric having a matrix potential and a water content;

providing a relationship between the water content and the matrix potential for the dielectric of the measuring cell;

detecting a change of the water content for the dielectric of the measuring cell caused by the moisture of the soil penetrating into the interior of said measuring cell;

determining the matrix potential for the dielectric by measurement of changes of permittivity of the dielectric of the measuring cell, based on the relationship between water content and matrix potential for the dielectric used and on the detected change in water content for the dielectric of the measuring cell; and using the determined matrix potential for the dielectric of the measuring cell as the matrix potential for the measured soil.

2. The method according to claim 1, characterized in that the dielectric of the measuring cell has a permittivity ratio which is smaller than or equal to 81.

3. The method according to claim 2, characterized in that the change of permittivity is detected by a capacitance measurement.

4. The method according to claim 2, characterized in that the change of permittivity is detected by measuring a velocity of propagation of an electromagnetic field in the dielectric, preferably based on a TDR measurement.

5. The method according to one of the preceding claims, characterized in that the dielectric is selectively chosen in accordance with a measurement range which is suitable for the soil to be measured.

6. A measuring instrument for measuring a matrix potential in a soil having moisture, comprising:

a measuring cell comprising a housing that includes, at least in certain sections thereof, a material permitting the moisture of the soil to penetrate into an interior of the housing, at least two electrodes which are arranged in said housing in spaced relationship with each other and a dielectric which fills the space between said electrodes and the inner wall of the housing; and a measurement evaluation circuit which detects a water content in the dielectric of the measuring cell by measurement of changes of permittivity of the dielectric and determines, based on said water content and based on a known relationship between the water content and the matrix potential of the dielectric used, the matrix potential prevailing in the dielectric, and which displays said matrix potential prevailing in the dielectric as a measuring result for the matrix potential in the soil.

7. The measuring instrument according to claim 6, characterized in that the measuring cell comprises a cylindrical housing and two bar electrodes extending parallel to one another in said housing.

8. The measuring instrument according to claim 6, characterized in that the dielectric used has a permittivity ratio which is smaller than or equal to 81.

9. The measuring instrument according to claim 6, characterized in that the evaluation circuit is, at least partially, arranged in the housing of the measuring cell.

10. The measuring instrument according to claim 6, characterized in that the evaluation circuit is implemented by means of a digital circuit and that the relationship between water content and matrix potential of the dielectric used is stored in the form of digital values.

11. The measuring instrument according to claim 6, characterized in that the evaluation circuit detects the water content of the dielectric by means of a measurement of capacitance between the electrodes.

12. The measuring instrument according to claim 6, characterized in that the evaluation circuit detects the water content by means of a TDR measurement in which an electromagnetic wave is transmitted through the dielectric along the electrodes.

13. The measuring instrument according to claim 6, characterized in that the dielectric of the measuring cell is adapted to be exchanged in accordance with a desired measuring range and that the evaluation circuit is designed such that it can be used for respective other dielectrics.

14. The measuring cell for measuring the matrix potential in a soil having moisture, comprising:

a housing comprising at least in certain sections thereof of a material permitting the moisture of the soil to penetrate into an interior of the housing;

at least two electrodes which are arranged in said housing in spaced relationship with each other; and a dielectric having a permittivity ratio which depends on the water content in the dielectric and which is smaller than or equal to 81, and filling the space between said electrodes and the inner wall of the housing the water content in the dielectric having a relationship to a matrix potential of the dielectric.

15. The measuring cell according to claim 14, characterized in that the measuring cell comprises a cylindrical housing and two bar electrodes extending parallel to one another in said housing.

16. The measuring cell according to claim 14, characterized in that, in an encapsulated part of the measuring cell, a measurement circuit is provided for processing signals supplied by the electrodes.

17. The measuring cell according to claim 14, characterized in that the housing of the measuring cell is formed, at least partially, by a polyamide net.

* * * * *